United States Patent [19]

Altland et al.

[11] 4,425,424
[45] Jan. 10, 1984

[54] DYE-FORMING COMPOSITIONS

[75] Inventors: Henry W. Altland; Raymond W. Ryan, Jr.; Phillip P. Senise, Jr.; Michael J. Lindstrom, all of Rochester, N.Y.

[73] Assignee: Eastman Kodak Company, Rochester, N.Y.

[21] Appl. No.: 390,488

[22] Filed: Jun. 21, 1982

Related U.S. Application Data

[63] Continuation-in-part of Ser. No. 366,886, Apr. 8, 1982, abandoned.

[51] Int. Cl.$^3$ .......................... G03C 1/52; G03C 1/68
[52] U.S. Cl. .................................. 430/270; 430/920; 430/332; 430/342; 430/338; 430/343; 430/285; 430/286; 430/281; 430/292
[58] Field of Search ............... 430/343, 338, 332, 270, 430/285, 286, 292, 281, 920, 342

[56] References Cited

U.S. PATENT DOCUMENTS

| | | |
|---|---|---|
| Re. 28,240 | 11/1974 | Jenkins . |
| 3,121,632 | 2/1964 | Sprague et al. . |
| 3,284,205 | 11/1966 | Sprague et al. . |
| 3,359,109 | 12/1967 | Harder et al. . |
| 3,364,030 | 1/1968 | Yembrick, Jr. . |
| 3,615,568 | 10/1971 | Jenkins . |
| 3,667,954 | 6/1972 | Itano et al. . |
| 4,139,390 | 2/1979 | Rauner et al. ................ 430/285 |
| 4,258,121 | 3/1981 | Kojima . |

FOREIGN PATENT DOCUMENTS 831466  1/1970  Canada .

OTHER PUBLICATIONS

*J. Amer. Chem. Soc.*, vol. 87, pp. 5186–5190 (1965).

*Primary Examiner*—Won H. Louie, Jr.
*Attorney, Agent, or Firm*—Dana M. Schmidt

[57] ABSTRACT

There is disclosed a radiation-sensitive composition comprising a leuco dye and a sulfonyloxy-N photooxidant that converts the leuco dye to a dye having a color different from that of its leuco form, when exposed to activating radiation. Improved print-out densities are obtained using this composition in image-forming methods.

18 Claims, No Drawings

DYE-FORMING COMPOSITIONS

RELATED APPLICATION

This application is a continuation-in-part application of U.S. Ser. No. 366,886, filed on Apr. 8, 1982, abandoned.

FIELD OF THE INVENTION

This invention relates to a dye-forming composition used, for example, in lithographic printing plate compositions to render visible the exposure given to the composition.

BACKGROUND OF THE INVENTION

Lithographic printing plate compositions frequently include a print-out composition comprising a leuco dye and a photooxidant (also called an accelerator or sensitizer in the literature). When the composition is exposed to activating radiation, the photooxidant converts the leuco dye to a form having a color different from that of the leuco dye. The use of the print-out composition in the printing plate is advantageous in that exposure levels given to the composition can be checked visually. If the exposures are determined to have been too low, or portions of the composition are seen to be unexposed, the plate can be re-exposed. To be effective for this purpose, the print-out composition must generate sufficient dye density upon exposure to be readily observed, without sacrificing significantly the speed of the plate. As is well known, the absorption by the photooxidant and/or the dye that prints up is selected so that it does not significantly interfere with the activation of the photopolymer.

Prior art print-out compositions have featured primarily carboxylic acid derivative photooxidants. Examples of such photooxidants, used in lithographic printing plates, are identified in U.S. Pat. No. 3,359,109, issued on Dec. 19, 1967. Many classes of useful leuco dyes are identified in the aforesaid patent. Useful photooxidants described in that patent include, N,N,O-triacylhydroxyl amines. A number of such photooxidants have been found to produce only faint print-out densities when used with, e.g., the tris(p-aminoaryl)methane leuco dyes appearing in the list of dyes in the '109 patent. Therefore, such photooxidants are of limited utility as the faint densities are difficult to observe.

Thus, prior to this invention there has been a need for a print-out composition that produces a readily detectable print-out density on exposure to activating radiation.

SUMMARY OF THE INVENTION

We have discovered that certain compounds derived from sulfonic acid are useful photooxidants which produce print-out densities superior to the print-out densities obtained with similar, conventional compounds derived from carboxylic acid.

Thus, there is advantageously featured a light-sensitive dye-forming composition capable of producing improved dye-forming densities. A further advantageous feature is that the improved print-out densities are achieved with an insignificant loss in the speed of any photopolymers included with the print-out composition.

These advantageous features are achieved, more specifically, by the use of an activating radiation-sensitive imaging composition comprising (1) a leuco form of a dye having one or more removable hydrogen atoms, the removal of which forms a compound colored differently from the leuco form and (2) a photooxidant capable of converting the leuco dye to the differently colored form when exposed to activating radiation. The composition is improved in that the photooxidant has the structural formula

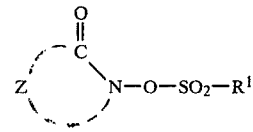

wherein
R$^1$ is a carbocyclic or heterocyclic ring containing from 5 to 10 ring atoms, and
Z represents the non-metallic atoms necessary to complete 1 or more rings containing from 5 to 17 ring atoms.

This composition is useful in an improved method of forming an image wherein increased print-out densities are produced.

Other features and advantages will become apparent upon reference to the following Description of the Preferred Embodiments.

DESCRIPTION OF THE PREFERRED EMBODIMENTS

The radiation-sensitive composition of this invention is described particularly in connection with a negative-working photopolymer useful to provide a lithographic printing plate composition. In addition, the invention is useful in any other composition wherein a visual print-out of the exposure is desired, for example, in metal working layouts, photoresists, and the like. The composition is useful with or without a negative-working or positive-working photopolymer present.

The composition of the invention comprises a leuco dye and a photooxidant as described above.

As used herein, "carbocyclic ring" and "heterocyclic ring" for R$^1$ of the photooxidant include both unsubstituted and substituted rings, such as aryl and substituted aryl such as phenyl, p-chlorophenyl, naphthyl, and the like. Other useful substituents on the carbocyclic or heterocyclic ring include halo-substituents such as bromo, and alkoxy such as methoxy. Useful heterocyclic rings include 2- or 3-thiophene; 2-or 3-furan; 2-, 3- or 4-pyridine; imidazole; triazole; and pyrazole.

Preferably Z represents the atoms necessary to provide a ring containing from 4 to 16 carbon atoms, producing, for example, a succinimide, glutarimide, phthalimide, a naphthalimide, or a pyridone or quinolone. Preferably, Z represents from 3 to 15 carbon atoms to form a cyclic moiety containing from 1 to 4 rings, optionally substituted with an oxy group adjacent to the nitrogen atom to form an additional ketone. Most preferably, Z represents such atoms which complete 1 to 2 rings.

Representative specific examples of photooxidants useful in this invention include N-(4-chlorobenzenesulfonyloxy)-1,8-naphthalimide; N-(4-chlorobenzenesulfonyloxy)phthalimide; N-benzenesulfonyloxyphthalimide; N-benzenesulfonyloxy-1,8-naphthalimide; N-benzenesulfonyloxy-2(1H)-pyridone; and N-benzenesulfonyloxy-2(1H)-quinolone.

The above noted photooxidants are synthesized using conventional procedures, of which the following are representative:

Preparation 1. Synthesis of N-Benzenesulfonyloxyphthalimide

A dichloromethane (50 ml) solution of triethylamine (3.1 g, 0.0306 mole) was slowly added to a stirred dichloromethane (50 ml) suspension of N-hydroxyphthalimide (5.0 g, 0.0306 mole) and benzenesulfonyl chloride (5.4 g, 0.0306 mole) at ice-bath temperature. The stirred reaction mixture was kept at ambient temperature for about 24 hours. The product was partitioned between dichloromethane and distilled water and the dichloromethane extract was dried with magnesium sulfate. Solvent was removed under reduced pressure and the residue was crystallized with ethyl acetate-n-pentane (2:1 v/v) to give 8.0 g (87%) of colorless crystals; mp 186°; mass spectrum M+ 303 (calcd. M+ 303).

|        | C    | H   | N   |
|--------|------|-----|-----|
| % calc.  | 55.4 | 3.0 | 4.6 |
| % found  | 55.4 | 2.6 | 5.1 |

Preparation 2. Synthesis of N-Benzenesulfonyloxy-1,8-naphthalimide

A stirred tetrahydrofuran (400 ml) mixture of N-hydroxy-1,8-naphthalimide (6.0 g, 0.028 mole), benzenesulfonyl chloride (5.0 g, 0.028 mole) and triethylamine (3.0 g, 0.030 mole) was kept at ambient temperature for 18 hours. After pouring this mixture into distilled water, the precipitated crude product was washed with distilled water and then recrystallized from tetrahydrofuran to give five grams of buff-colored crystals; mp 211°-213° C.

|        | C    | H   | N   |
|--------|------|-----|-----|
| % calc.  | 61.2 | 3.1 | 4.0 |
| % found  | 61.0 | 3.3 | 4.3 |

Preparation 3. Synthesis of N-(4-Chlorobenzenesulfonyloxy)phthalimide

In a 3-neck, 500 ml round bottom flask, dichloromethane (100 ml) was added to 16.3 g (0.10 mole) of N-hydroxyphthalimide. To this was added 21.1 g (0.10 mole) of 4-chlorobenzenesulfonyl chloride. To this suspension at ice-bath temperature, with slow stirring, was added dropwise 10.1 g (0.10 mole) of triethylamine in 50 ml of dichloromethane. This stirred reaction mixture was held at ambient temperature for 72 hours. Then, more dichloromethane and 100 ml of water were added to the suspension. The dichloromethane extract was dried with magnesium sulfate. Solvent was removed under reduced pressure and the residue was recrystallized from 500 ml of ethyl acetate to give 10.2 g of a white solid, mp 178°-180° C.

|        | C    | H   | N   | S   | Cl   |
|--------|------|-----|-----|-----|------|
| % calc.  | 49.8 | 2.4 | 4.1 | 9.5 | 10.5 |
| % found  | 50.0 | 2.1 | 4.4 | 8.9 | 10.6 |

Preparation 4. Synthesis of N-(4-Chlorobenzenesulfonyloxy)-1,8-naphthalimide To a stirred suspension of N-hydroxy-1,8-naphthalimide (10.0 g, 0.047 mole) and of triethylamine (4.7 g, 0.046 mole) in tetrahydrofuran (150 ml) was added 4-chlorobenzenesulfonyl chloride (10.0 g, 0.047 mole). This stirred mixture was kept at ambient temperature for 18 hours. The mixture was poured into distilled water and the precipitated solid was washed with distilled water and then was air-dried. The 1,8-naphthalimide was crystallized once from p-dioxane to give 8.0 g (44%) of colorless crystals; mp 235°-240° C.; mass spectrum M+ 387 (calcd M+ 387).

|        | C    | H   | N   | Cl  |
|--------|------|-----|-----|-----|
| % calc.  | 55.8 | 2.5 | 3.6 | 9.0 |
| % found  | 55.6 | 2.2 | 3.9 | 8.7 |

Any leuco dye that converts to a differently colored form upon the removal of one or more hydrogen atoms is useful. Dyes that do not absorb significantly at the wavelengths used to activate the photopolymer are preferred. Most preferred are those leuco dyes in which the removable hydrogen(s) are not sterically hindered. Thus, useful leuco dyes are available from the classes set forth in the aforesaid U.S. Pat. Nos. 3,359,109 or in 4,139,390, issued Feb. 13, 1979. Included are aminotriarylmethanes, for example, 4,4',4"-methylidenetris(N,N-dipropylaniline) and 4,4',4"-methylidenetris(N,N-dimethylaniline); aminoxanthenes such as 3,6-bis(dimethylamino)-9-(p-dimethylaminophenyl)xanthene and 3,6-bis(diethylamino-9-(p-dimethylaminophenyl)xanthene; aminothioxanthenes; aminophenoxazines; aminophenothiazines; aminodihydrophenazines, such as 3,6-bis(dimethylamino)-9-(p-dimethylaminophenyl)phenazine and 3,7-bis(dimethylamino)-5,10-dihydro-5-phenylphenazine; aminodiphenylmethanes such as 1,1-bis(p-dimethylaminophenyl)methane; leuco indamines; aminohydrocinnamic acids such as 4-(p-chloroanilino)-α,β-dicyanohydrocinnamic acid, methyl ester and 4-anilino-α,β-dicyanohydrocinnamic acid, methyl ester; hydrazines such as 1-(2-naphthyl)-2-phenylhydrazine and 1-(p-dimethylaminophenyl)-2-(2-pyridyl)hydrazine; leuco indigoid dyes; amino-2,3-dihydroanthraquinones; and phenethylanilines such as N-(2-cyanoethyl)-p-phenethylaniline and N,N-diethyl-p-phenylethylaniline.

The composition of the invention is especially useful in a lithographic printing plate composition comprising a photopolymer, and most preferably a negative-working photocrosslinkable polymer such as those described in the aforesaid U.S. Pat. No. 4,139,390. Particularly useful examples include negative-working polyesters, polycarbonates, and polysulfonates that comprise recurring units containing the light-sensitive moiety

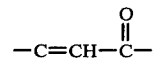

as an integral part of the polymer backbone. Such lithographic plates are formed by coating, in a conventional manner, the composition containing the leuco dye, photooxidant and photopolymer, onto a suitable support from a suitable solvent. Optionally, a photosensitizer is included, particularly when using negative-working photopolymers. Useful examples of photosensitizers for the photopolymer, additional addenda for the composition, supports and solvents include those described in the aforesaid U.S. Pat. No. 4,139,390, the details of which are expressly incorporated herein by reference.

A negative-working lithoplate composition, after being coated and dried on the support, is used by exposing it to activating radiation that crosslinks the polymer and removes hydrogen atoms from the leuco dye in the exposed areas to print out in those areas. Development of the photopolymer is achieved by removing the non-exposed areas with a suitable developer. The developer used is a conventional developer, selected in accordance with the photopolymer used in the lithographic composition. For the polyesters, polycarbonates, and polysulfonates noted above, a particularly useful developer is one comprising:

| | |
|---|---|
| 4-Butyrolactone | 1000.0 ml |
| A nonionic ethylene oxide-ester condensate available under the trademark "Zonyl A" from the E. I. duPont deNemours Co. | 10.0 ml |
| Methyl Abietate | 10.0 ml |
| Hydrogenated rosin available under the trademark "Staybelite" resin from Hercules Powder Co. | 1.0 g |
| Glycerol | 100.0 ml |
| Water | 100.0 ml |
| Phosphoric Acid | 25.0 ml |
| Triethanolamine | 12.5 ml |

Unexpectedly, the composition of the invention has been found to produce print-out densities that are superior to those produced using the carboxylic acid derivatives of the same photooxidants. When combined with a photopolymer and photosensitizer to produce a lithographic printing plate composition, no significant difference in speed of the photopolymer is produced when compared with the carboxylic acid derivatives.

EXAMPLES

The following examples further illustrate the invention.

EXAMPLES 1-3

To demonstrate the superior print-out densities of the invention, the following lithographic printing plate composition was prepared: Polyester of 1,4-di-($\beta$-hydroxyethoxy)cyclohexane with p-phenylenediacrylic acid, comprising the recurring unit:

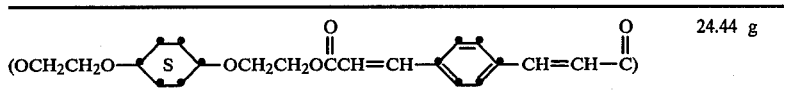

| | |
|---|---|
| (19.48 weight % in 1,2-dichloroethane) Polystyrene available under the trademark Piccolastic A-50 from Pennsylvania Industrial Chemicals Corp. (binder) | 1.65 g |
| 2-[Bis(2-furoyl)methylene]-1-methylnaphtho-[1,2-d]thiazoline (BFT) (photosensitizer for the polyester) | 0.14 g |
| 2,6-Di-tert butyl-p-cresol (stabilizer) | 0.19 g |
| Dihydroanhydropiperidinohexose reductone (antioxidant) | 0.02 g |
| 4,4′,4″-methylidenetris(N,N—dipropylaniline) (leuco dye) | 0.23 g |
| Monastral Red B pigment (7.80% in 1,2-dichloroethane) (obtained from E. I. duPont deNemours and Co.) | 24.41 g |
| MODAFLO (1% in 1,2-dichloroethane) (surfactant) | 0.87 g |
| Photooxidant of Table I | 0.43 to 0.62 g |
| 1,2-Dichloroethane (solvent) | 198.06 g |

TABLE I

| Example | Photooxidant Structure | Photooxidant Name | Amount |
|---|---|---|---|
| Control A | None | — | None |
| Control B | (structure shown) | N—Benzoyloxyphthalimide (U.S. Pat. No. 3,359,109, col. 5) | 0.43 g |

TABLE I-continued

| Example | Photooxidant Structure | Photooxidant Name | Amount |
|---|---|---|---|
| 1 | [structure] | N—Benzenesulfonyloxy-phthalimide | 0.48 g |
| Control C | [structure] | N—(4-chlorobenzoyloxy)-phthalimide | 0.48 g |
| 2 | [structure] | N—(4-chlorobenzenesulfonyl-oxy)phthalimide | 0.54 g |
| Control D | [structure] | N—(4-chlorobenzoyloxy)-1,8-naphthalimide | 0.56 g |
| 3 | [structure] | N—(4-chlorobenzenesulfonyl-oxy)-1,8-naphthalimide | 0.62 g |

All photooxidants were at equal molar amounts.

Coatings were prepared on a drum coating machine at a total dry coverage of 10.8 mg/dm², on a support comprising an anodized aluminum support having 0.43 mg/dm² of carboxylmethyl cellulose/zinc acetate sub- bing. Uniform coatings of excellent quality having no evidence of pigment agglomeration were obtained. All coating solutions showed good pigment stability upon standing. To determine print-out, samples of each coating were flashed on a 2000-watt NuArc pulsed Xenon exposing frame for 60 seconds. Reflection densities of unprocessed samples were measured through a Wratten 106 filter on a MacBeth RD-514 densitometer. ΔD or a difference density was calculated as the difference between the exposed plate density and the unexposed background density.

To determine sensitometric response, a sample of each coating was similarly exposed for 60 seconds in a NuArc exposure unit through a Kodak T-14 wedge (0.15 density increments). Washout processing was accomplished by wiping the plates with a cotton swab soaked with a developer of which the preferred composition is set forth above.

After development, the imaged samples were analyzed for lithographic sensitometric speed response using CR speeds based upon reflection densities, for each T-14 step exposure, measured through a Wratten 58 green filter on a Macbeth RD-514 densitometer. CR speed values were calculated using a plot of reflection density versus exposure. A 15 CR unit change is equivalent to a 0.15 log E change. Samples of each coating were incubated for 2 weeks at 50° C. and 50% RH, after which print-out and sensitometric tests were again run on freshly exposed and processed samples. Table II lists the results of these tests on fresh samples and on incubated samples.

TABLE II

Print-Out Density and CR Speed Comparisons

| Example | Print-Out Difference Density (ΔD) | | Relative Speed (CR) | |
|---|---|---|---|---|
|  | fresh | inc. | fresh | inc. |
| Control A | 0.01 | 0.01 | 116 | 127 |
| Control B | 0.02 | 0.02 | 116 | 122 |
| 1 | 0.12 | 0.08 | 107 | 115 |
| Control C | 0.05 | 0.03 | 108 | 110 |
| 2 | 0.11 | 0.08 | 103 | 116 |
| Control D | 0.04 | 0.02 | 110 | 113 |
| 3 | 0.12 | 0.09 | 102 | 112 |

Those results show a consistently higher print-out density difference for the arylsulfonyloxy compounds over the corresponding aroyloxy control compounds comprising conventional photooxidants. The CR speeds of the composition of the invention are also in an acceptable range.

EXAMPLES 4–7

Use with Other Leuco Dyes

The procedure of Examples 1–3 was repeated using the photooxidant of Example 3 and equimolar amounts of the compounds of Table III as the leuco dye. Development, prior to relative speed measurement, was by machine using a different but similar developer solution. The support was given a slightly different subbing treatment. Neither the different subbing nor the different developer is expected to affect print-out densities. Control D was repeated in each example, as controls D(4), D(5), D(6) and D(7), respectively. The results, measured fresh only, appear in Table IV. The Comparative Example was included to illustrate a leuco dye that was found not to be useful, possibly because of steric hindrance of the removable hydrogen.

TABLE III

| Example | Leuco Dye |
|---|---|
| 4 | 1,1-bis(p-dimethylaminophenyl)methane |

TABLE III-continued

| Example | Leuco Dye |
|---|---|
| 5 | $Q^1$ = CH$_3$O—, $Q^2$ = CH$_3$O— (structure shown) |
| 6 | $Q^1$ = CH$_3$—, $Q^2$ = CH$_3$O— |
| 7 | $Q^1$ = CH$_3$, $Q^2$ = N(C$_2$H$_5$)(CH$_2$CH$_2$—N(H)—SO$_2$—CH$_3$) |
| Comp. Ex. | 1,1-bis(2-methyl-4-diethylaminophenyl)butane |

Structure (Examples 5–7):

$$Q^2-\underset{\text{(ring)}}{Q^1}-N(H)-\text{(ring)}-N(H)-SO_2-\text{(2,6-diisopropyl-4-propylphenyl)}$$

with H—N—C(=O)—C$_7$H$_{15}$ substituent on middle ring; wherein iPr = isopropyl

TABLE IV

| Example | ΔD | Relative Speed (CR)[1] |
|---|---|---|
| Control D(4) | .01 | 119 |
| 4 | .05 | 116 |
| Control D(5) | .00 | 112 |
| 5 | .03 | 107 |
| Control D(6) | .01[2] | 116 |
| 6 | .01[2] | 110 |
| Control D(7) | .02 | 85[3] |
| 7 | .04 | 82[3] |
| Comp. Ex. | .00 | 113 |

[1]The speeds of each Control D differ from pair to pair, primarily because different dye densities of the print-out composition affect the speed of the plate differently.
[2]No difference could be seen in this comparison, primarily because the colored form of the leuco dye (red-orange) gave insufficient contrast with the red pigment of the plate composition. If no pigment is used, superior performance using the photooxidant of Example 6 is expected, compared to the control.
[3]The reduction in relative speeds for this pair, compared to the previous pairs, is believed to be due to the green print-up dye that results, acting to absorb some light that would otherwise activate the sensitizer of the photopolymer. These CR speeds are still considered to be adequate so that the leuco dye of Example 7 is acceptable.

EXAMPLE 8

To determine the photooxidant behavior of certain quinolones, the following composition was prepared:

TABLE V

| | |
|---|---|
| Polyester of Example 1 (16.2 weight % solution) | 300 g |
| 2,6-di-t-butyl-p-cresol (stabilizer) | 1.5 g |
| BFT photosensitizer of Example 1 | 3.3 g |
| leuco propyl violet (leuco dye) | 1.5 g |
| photooxidant of Table VI | — |
| dihydroanhydropiperidinohexose reductone [stabilizer for photooxidant] | 0.15 g |
| Monastral Blue BF Pigment (7.5 weight % in 1,2-dichloroethane) (obtained from E. I. DuPont deNemours & Co.) | 53.2 g |
| fluorochemical surfactant obtained from 3M under the trademark "FC-430" | 0.2 g |
| 1,2-dichloroethane (solvent) | 883 g |

TABLE VI

| Example | Photooxidant | Amount |
| --- | --- | --- |
| Control E | 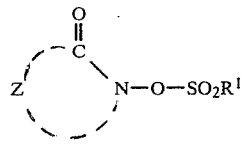 | 2.14 g |
| 8 | 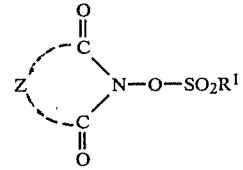 | 2.43 g |

These two compositions were coated at about 14.66 mg/dm² on a support similar to that of Example 1. To determine print-out density, the coatings were exposed to the exposing unit of Example 1 for about 60 seconds, and ΔD densities were measured as in Example 1. The results, measured on fresh samples, appear in Table VII:

TABLE VII

| Example | ΔD |
| --- | --- |
| Control F | 0.01 |
| 8 | 0.05 |

These results indicated a superior ΔD when the N-oxy-substituent was the sulfonyl rather than the carbonyl.

EXAMPLE 9

The procedure of Example 8 was repeated, except that the photooxidants were the pyridones of Table VIII, the amounts of the ingredients were scaled down and no pigment was included. Molar equivalent weights were used for the photooxidants.

TABLE VIII

| Example | Photooxidant | Amount | ΔD |
| --- | --- | --- | --- |
| Control G | N—O—C(=O)—C$_6$H$_5$ (pyridone) | 0.18 g in 100 cc of solution | 0.03 |
| 9 | N—O—SO$_2$—C$_6$H$_5$ (pyridone) | molar equivalent weight | 0.13 |

The invention has been described in detail with particular reference to preferred embodiments thereof, but it will be understood that variations and modifications can be effected within the spirit and scope of the invention.

What is claimed is:

1. In an activating radiation-sensitive imaging composition comprising (1) a leuco form of a dye having one or more removable hydrogen atoms the removal of which forms a compound colored differently from the leuco form and (2) a photooxidant capable of converting said leuco dye to said differently colored form when said composition is exposed to activating radiation,
the improvement wherein said photooxidant has the structural formula $$\begin{array}{c} O \\ \| \\ \diagup C \diagdown \\ Z \quad \quad N-O-SO_2R^1 \\ \diagdown \quad \diagup \end{array}$$

wherein
$R^1$ is a carbocyclic or heterocyclic ring containing from 5 to 10 ring atoms, and
Z represents the non-metallic atoms necessary to complete 1 or more rings containing from 5 to 17 ring atoms,
said photooxidant being present in an amount effective to provide an improved difference density of said colored form compared to the difference density produced by the same composition lacking said photooxidant.

2. In an activating radiation-sensitive imaging composition comprising (1) a leuco form of a dye having one or more removable hydrogen atoms the removal of which forms a compound colored differently from the leuco form and (2) a photooxidant capable of converting said leuco dye to said differently colored form when said composition is exposed to activating radiation,
the improvement wherein said photooxidant has the structural formula $$\begin{array}{c} O \\ \| \\ \diagup C \diagdown \\ Z \quad \quad N-O-SO_2R^1 \\ \diagdown C \diagup \\ \| \\ O \end{array}$$

wherein
$R^1$ is a carbocyclic or heterocyclic ring containing from 5 to 10 ring atoms, and
Z represents the non-metallic atoms necessary to complete 1 or more rings containing from 5 to 17 ring atoms,
said photooxidant being present in an amount effective to provide an improved difference density of said colored form compared to the difference density produced by the same composition lacking said photooxidant.

3. A composition as defined in claim 1 or 2, wherein said leuco form of said dye is a leuco aminotriarylmethane dye.

4. A composition as defined in claim 1 or 2, wherein $R^1$ is aryl.

5. A composition as defined in claim 1 or 2, wherein $R^1$ is phenyl.

6. A composition as defined in claim 1 or 2, wherein $R^1$ is p-chlorophenyl.

7. A composition as defined in claim 1, wherein Z comprises from 3 to 15 carbon atoms.

8. A composition as defined in claim 1 or 2, wherein said photooxidant is a phthalimide.

9. A composition as defined in claim 1 or 2, wherein said photooxidant is a naphthalimide.

10. A composition as defined in claim 1 or 2, wherein said photooxidant is N-(4-chlorobenzenesulfonyloxy)-1,8-naphthalimide.

11. A composition as defined in claim 1 or 2, wherein said photooxidant is N-(4-chlorobenzenesulfonyloxy)phthalimide.

12. A composition as defined in claim 1 or 2, wherein said photooxidant is N-benzenesulfonyloxyphthalimide.

13. A composition as defined in claim 1 or 2, wherein said photooxidant is N-benzenesulfonyloxy-1,8-naphthalimide.

14. A composition as defined in claim 1 or 2, and further including a negative-working or positive-working photopolymer and optionally a photosensitizer.

15. In an imaging element useful to obtain a lithographic printing plate, comprising a support, and on the support, a composition comprising a negative-working photopolymer, a photosensitizer, a leuco form of a dye having one or more removable hydrogen atoms the removal of which forms a compound colored differently from the leuco form and a photooxidant capable of converting said leuco dye to said differently colored form when exposed to activating radiation, the improvement wherein said photooxidant has the structural formula

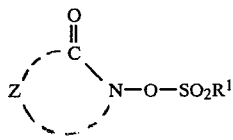

wherein $R^1$ is a carbocyclic or heterocyclic ring containing from 5 to 10 ring atoms, and Z represents the non-metallic atoms necessary to complete 1 or more rings containing from 5 to 17 ring atoms, said photooxidant being present in an amount effective to provide an improved difference density of said colored form compared to the difference density produced by the same composition lacking said photooxidant.

16. In an imaging element useful to obtain a lithographic printing plate, a comprising a support, and on the support, a composition comprising a negative-working photopolymer, a photosensitizer, a leuco form of a dye having one or more removable hydrogen atoms the removal of which forms a compound colored differently from the leuco form and a photooxidant capable of converting said leuco dye to said differently colored form when said composition is exposed to activating radiation, the improvement wherein said photooxidant has the structural formula

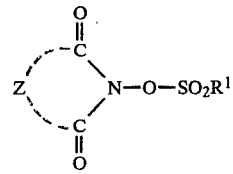

wherein $R^1$ is a carbocyclic or heterocyclic ring containing from 5 to 10 ring atoms, and Z represents the non-metallic atoms necessary to complete 1 or more rings containing from 5 to 17 ring atoms, said photooxidant being present in an amount effective to provide an improved difference density of said colored form compared to the difference density produced by the same composition lacking said photooxidant.

17. In a method of forming an image, comprising the step of imagewise exposing to activating radiation a composition comprising a print-out leuco dye having one or more removable hydrogen atoms the removal of which forms a compound colored differently from the leuco form, the improvement wherein the print-out density of said leuco dye is increased by means of a photooxidant having the structural formula

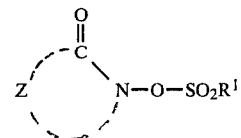

wherein $R^1$ is a carbocyclic or heterocyclic ring containing from 5 to 10 ring atoms, and Z represents the non-metallic atoms necessary to complete 1 or more rings containing from 5 to 17 ring atoms, said photooxidant being present in an amount effective to provide an improved difference density of said colored form compared to the difference density produced by the same composition lacking said photooxidant.

18. In a method of forming an image, comprising the step of imagewise exposing to activating radiation a composition comprising a print-out leuco dye having one or more removable hydrogen atoms the removal of which forms a compound color differently from the leuco form, the improvement wherein the print-out density of said leuco dye is increased by means of a photooxidant having the structural formula

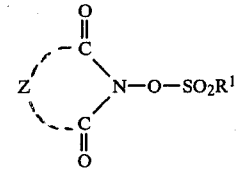

wherein $R^1$ is a carbocyclic or heterocyclic ring containing from 5 to 10 ring atoms, and Z represents the non-metallic atoms necessary to complete 1 or more rings containing from 5 to b 17 ring atoms, said photooxidant being present in an amount effective to provide an improved difference density of said colored form compared to the difference density produced by the same composition lacking said photooxidant.

* * * * *

UNITED STATES PATENT AND TRADEMARK OFFICE
CERTIFICATE OF CORRECTION

PATENT NO. : 4,425,424
DATED : January 10, 1984
INVENTOR(S) : Henry W. Altland et al It is certified that error appears in the above-identified patent and that said Letters Patent are hereby corrected as shown below:

Title page, the title, reading "DYE-FORMING COMPOSITIONS", should read --NOVEL DYE-FORMING COMPOSITIONS--.

Col. 1, line 1, the title reading "DYE-FORMING COMPOSITIONS", should read --NOVEL DYE-FORMING COMPOSITIONS--.

Signed and Sealed this

Twelfth Day of November 1985

[SEAL]

Attest:

DONALD J. QUIGG

Attesting Officer

Commissioner of Patents and Trademarks